US010527533B2

(12) United States Patent
Lambert et al.

(10) Patent No.: US 10,527,533 B2
(45) Date of Patent: Jan. 7, 2020

(54) MOISTURE AND VOLATILES ANALYZER

(71) Applicant: CEM Corporation, Matthews, NC (US)

(72) Inventors: Joseph Lambert, Charlotte, NC (US); David Deese, Indian Trail, NC (US); William Jennings, Wingate, NC (US)

(73) Assignee: CEM Corporation

( * ) Notice: Subject to any disclaimer, the term of this patent is extended or adjusted under 35 U.S.C. 154(b) by 0 days.

(21) Appl. No.: 16/190,356

(22) Filed: Nov. 14, 2018

(65) Prior Publication Data

US 2019/0078988 A1 Mar. 14, 2019

Related U.S. Application Data

(63) Continuation of application No. 14/930,754, filed on Nov. 3, 2015.

(Continued)

(51) Int. Cl.
*G01N 5/04* (2006.01)
*H05B 6/64* (2006.01)
(Continued)

(52) U.S. Cl.
CPC ............... *G01N 5/045* (2013.01); *G01J 5/10* (2013.01); *H05B 6/64* (2013.01); *H05B 6/645* (2013.01);
(Continued)

(58) Field of Classification Search
CPC ...................................................... H05B 6/745
See application file for complete search history.

(56) References Cited

U.S. PATENT DOCUMENTS

| 3,909,598 A | 9/1975 | Collins |
| 4,219,716 A * | 8/1980 | Kaufman, Jr. ........ F24C 15/027 |
| | | 126/19 M |

(Continued)

FOREIGN PATENT DOCUMENTS

| CA | 1227543 | 9/1987 |
| CN | 2117606 | 9/1992 |

(Continued)

OTHER PUBLICATIONS

Top New Pittcon Products, Mar. 15, 2016; https://instrumentbusinessoutlook.com/article/top-new-pit/con-products/ accessed May 28, 2018; 3 pages.

(Continued)

*Primary Examiner* — Justin N Olamit
(74) *Attorney, Agent, or Firm* — Summa PLLC (57) ABSTRACT

A volatile content analysis instrument is disclosed that includes a cavity and a microwave source positioned to produce and direct microwaves into the cavity at frequencies other than infrared frequencies. A balance is included with at least the balance pan (or platform) in the cavity. An infrared source is positioned to produce and direct infrared radiation into the cavity at frequencies other than the microwave frequencies produced by the microwave source. A lens is positioned between the infrared source and the balance pan for more efficiently directing infrared radiation to a sample on the balance pan. The lens has dimensions that preclude microwaves of the frequencies produced by the source and directed into the cavity from leaving the cavity.

1 Claim, 11 Drawing Sheets

Related U.S. Application Data (60) Provisional application No. 62/217,375, filed on Sep. 11, 2015.

(51) Int. Cl.
*H05B 6/76* (2006.01)
*G01J 5/10* (2006.01)

(52) U.S. Cl.
CPC ......... *H05B 6/6464* (2013.01); *H05B 6/6482* (2013.01); *H05B 6/76* (2013.01); *H05B 2206/046* (2013.01)

(56) References Cited

U.S. PATENT DOCUMENTS

| | | | |
|---|---|---|---|
| 4,291,775 A | 9/1981 | Collins | |
| 4,438,500 A | 3/1984 | Collins | |
| 4,457,632 A | 7/1984 | Collins | |
| 4,663,508 A * | 5/1987 | Ishimura | H05B 6/6411 126/197 |
| 4,681,996 A | 7/1987 | Collins | |
| 4,771,154 A * | 9/1988 | Bell | F24C 7/06 219/399 |
| 4,956,538 A * | 9/1990 | Moslehi | G01J 5/0003 219/121.6 |
| 6,227,041 B1 | 5/2001 | Collins | |
| 6,288,379 B1 | 9/2001 | Greene | |
| 6,302,577 B1 * | 10/2001 | Jennings | G01G 19/52 177/145 |
| 6,521,876 B2 * | 2/2003 | Jennings | G01N 5/045 219/746 |
| 6,566,637 B1 | 5/2003 | Revesz | |
| 6,900,422 B2 * | 5/2005 | Herold | H05B 6/6426 174/392 |
| 7,581,876 B2 * | 9/2009 | Revesz | G01N 5/045 219/680 |
| 7,617,717 B2 | 11/2009 | Luchinger | |
| 8,637,823 B2 | 1/2014 | Giebeler | |
| 9,804,030 B2 * | 10/2017 | Sikora | G01J 5/0896 |
| 9,853,413 B2 * | 12/2017 | Kim | H01S 5/02212 |
| 2004/0020920 A1 | 2/2004 | Herold | |
| 2004/0089806 A1 | 5/2004 | Murakami | |
| 2013/0265051 A1 | 10/2013 | Collins | |

FOREIGN PATENT DOCUMENTS

| | | |
|---|---|---|
| CN | 2259626 | 8/1997 |
| CN | 201837570 | 5/2011 |
| CN | 202947942 | 5/2013 |
| CN | 203101213 | 7/2013 |
| CN | 103308417 | 9/2013 |
| CN | 203231949 | 10/2013 |
| CN | 203929556 | 11/2014 |
| CN | 204064843 | 12/2014 |
| CN | 104395742 | 3/2015 |
| EP | 1879014 | 8/1916 |
| EP | 1297327 | 2/2010 |
| EP | 1114308 | 8/2014 |
| EP | 1214582 | 2/2015 |
| GB | 1114459 | 5/1968 |
| GB | 2152790 | 8/1985 |
| GB | 2278202 | 11/1994 |
| JP | S58204336 | 11/1983 |
| JP | H02115750 | 4/1990 |
| JP | H0389139 | 4/1991 |
| JP | H03134541 | 6/1991 |
| JP | H0593684 | 4/1993 |
| JP | H06281556 | 10/1994 |
| JP | H09297095 | 11/1997 |
| JP | H10267821 | 10/1998 |

OTHER PUBLICATIONS

Smart 6(TM) Peer Reviews; CEM Corporation Smart 6(TM) Brochure; http://cem.com/en/smart-6-brochure; accessed May 28, 2018; 1 page.

Pittcon Special Report: CEM Change the World of Moisture, Solids Analysis; Mar. 9, 2016; https://www.rdmag.com/article/2016/03/pittcon-social-report-cem-changes-world-moisture-solids-analysis; accessed Mar. 28, 2018; 4 pages.

CEM Smart 6(TM) Brochure—Comparison Tables pp. 4-5; http://cem.com/en/smart-6-brochure; accessed May 28, 2018; 8 pages.

* cited by examiner

MOISTURE AND VOLATILES ANALYZER

RELATED APPLICATIONS

This application is a continuation of Ser. No. 14/930,754 filed on Nov. 3, 2015 which claims priority to Ser. No. 62/217,375 filed on Sep. 11, 2015.

BACKGROUND

The present invention relates to instrumentation for conducting loss-on-drying analysis of moisture and volatile content for a wide variety of materials.

Measuring the moisture content, or the volatile content, or both of materials is a necessary, valuable, frequent, and repetitive task in many circumstances.

For example, in a manufacturing setting, the measurement of sample volatile content may be an important step in a quality control procedure. If the time for conducting the analysis is long, then poor quality samples may not be detected for several hours or days. In this circumstance, the manufacturing facility may have continued producing the lower quality product throughout the time necessary for conducting the test. Accordingly, a large quantity of poor quality material may have been produced before the quality problem was discovered. Such a delay often leads to cost overruns and manufacturing delays, as the poor quality product may require disposal and the manufacturing process must begin again.

In its simplest form, determining volatile or moisture content consists of weighing a representative sample of material, drying the material, then re-weighing the material to ascertain the losses on drying and, consequently, the initial volatile content of the sample. Convective, hot-air ovens, which are often used for this task, can be relatively slow to bring the sample to "oven-dry" equilibrium. Such devices can also be expensive to operate as they inefficiently consume energy. These problems lessen the utility of hot-air devices for volatile analysis.

Drying certain substances using microwave energy to determine volatile or moisture content is generally convenient and precise. The term "microwaves" refers to that portion of the electromagnetic spectrum between about 300 and 300,000 megahertz (MHz) with wavelengths of between about one millimeter (1 mm) and one meter (1 m). These are, of course, arbitrary boundaries, but help quantify microwaves as falling below the frequencies of infrared (IR) radiation and above those referred to as radio frequencies. Similarly, given the well-established inverse relationship between frequency and wavelength, microwaves have longer wavelengths than infrared radiation, but shorter than radio frequency wavelengths. Additionally, a microwave instrument incorporating a micro-processor can monitor the drying curve (weight loss vs. time) of a sample and can predict the final dried weight (and thus the original moisture content) based on an initial portion of the drying curve. Such analyses may be conducted in about one to three minutes for samples that contain free water.

More importantly, microwave drying to measure moisture content is usually faster than equivalent hot-air methods. Microwaves are, however, selective in their interaction with materials, a characteristic that potentially leads to non-uniform heating of different samples and associated problems. Stated differently, the rapid manner in which microwaves tend to interact with certain materials, which is an obvious advantage in some circumstances, can cause secondary heating of other materials that is disadvantageous (at least for volatile or moisture measurement purposes).

Additionally, microwaves interact with materials in a fashion known as "coupling," i.e., the response of the materials ("the load") to the microwave radiation. Some materials do not couple well with microwave energy, making drying or other volatile removal techniques difficult or imprecise. Other materials couple well when their moisture content, or content of other microwave-responsive materials (e.g., alcohols and other polar solvents), is high. As they dry under the influence of microwaves, however, they couple less and less effectively; i.e., the load changes. As a result, the effect of the microwaves on the sample becomes less satisfactory and more difficult to control. In turn, the sample can tend to burn rather than dry, or degrade in some other undesired fashion. Both circumstances, of course, tend to produce unsatisfactory results.

As another factor, volatiles, such as "loose" water (i.e., not bound to any compound or crystal) respond quickly to microwave radiation, but "bound" water (i.e., water of hydration in compounds such as sodium carbonate monohydrate, $Na_2CO_3 \cdot H_2O$) and nonpolar volatiles (e.g., low molecular weight hydrocarbons and related compounds) are typically unresponsive to microwave radiation. Instead, such bound water or other volatiles must be driven off thermally; i.e., by heat conducted from the surroundings.

Thus, microwaves can help remove bound water from a sample when the sample contains other materials that are responsive to microwaves. In such cases, the secondary heat generated in (or by) the microwave-responsive materials can help release bound water. The nature of microwave radiation is such, however, that not all such materials or surroundings may be heated when exposed to microwaves. Thus, loss-on-drying measurements using microwaves are typically less satisfactory for determining bound water than are more conventional heating methods.

In order to take advantage of the speed of microwave coupling for samples that do not readily absorb or couple with microwaves, techniques have been incorporated in which a sample is placed on a material that absorbs microwaves and becomes heated in response to those microwaves (often referred to as a susceptor). U.S. Pat. No. 4,681,996 is an example of one such technique. As set forth therein, the goal is for the thermally-responsive material to conductively heat the sample to release the bound water. Theoretically, a truly synergistic effect should be obtained because the thermally heated material heats the sample to remove bound water while the free water responds to, and is removed by, the direct effect of the microwaves.

Susceptor techniques, however, are less successful in actual practice. As one disadvantage, the necessary susceptors are often self-limiting in temperature response to microwaves, and thus different compositions are required to obtain different desired temperatures.

As another disadvantage, the predictability of a susceptor's temperature response can be erratic. As known to those familiar with content analysis, certain standardized drying tests are based upon heating a sample to, and maintaining the sample at, a specified temperature for a specified time. The weight loss under such conditions provides useful and desired information, provided the test is run under the specified conditions. Thus, absent such temperature control, microwave techniques may be less attractive for such standardized protocols.

As another disadvantage, the susceptor may tend to heat the sample unevenly. For example, in many circumstances, the portion of the sample in direct contact with the susceptor may become warmer than portions of the sample that are not in such direct contact. Such uneven temperatures may lead to incomplete removal of bound moisture as well as inaccurate loss-on-drying analyses.

Bound water may be removed in some circumstances by applying infrared radiation to a sample. Infrared radiation succeeds in driving off bound water (as well as any free water) by raising the temperature of the sample to an extent that overcomes the activation energy of the water-molecule bond. Infrared drying is also faster than oven drying for many samples. Nevertheless, infrared radiation tends to heat moisture-containing samples relatively slowly as compared to microwaves. Furthermore, infrared radiation typically heats the surface (or near surface) of the material following which the heat conducts inwardly; and typically takes time to do so. Infrared radiation will, however, heat almost all materials to some extent, and thus it offers advantages for materials that do not couple with microwaves.

Merely using two devices (e.g., one microwave and one infrared) to remove the two types of volatiles does not provide a satisfactory solution to the problem because moving the sample between devices typically results in at least some cooling, some loss of time (efficiency), the potential to regain moisture (under principles of physical and chemical equilibrium), and an increase in the experimental uncertainty (accuracy and precision) of the resulting measurement. Furthermore, if a sample is moved from a first balance in a microwave cavity to a second (separate) balance exposed to infrared radiation, the tare on the first balance would be meaningless with respect to the use of the second balance.

U.S. Pat. No. 7,581,876 addresses a number of these issues successfully. As set forth herein, the present invention further increases both heating efficiency and accuracy of temperature measurement.

SUMMARY

In a first aspect, the invention is a volatile content analysis instrument that includes a cavity and a balance with at least the balance pan (or platform) in the cavity. An infrared source is positioned to direct infrared radiation into the cavity, with a lens between said infrared source and said balance pan for more efficiently directing infrared radiation to a sample on said balance pan.

The term "lens" is used herein in the sense of an item or device that directs or focuses radiation, including frequencies (wavelengths) other than visible light, such as infrared or microwave radiation. The reflective collimator described and claimed herein falls within this dictionary definition.

In another aspect, the invention is a volatile content analysis instrument that includes a cavity and a microwave source positioned to produce and direct microwaves into the cavity at frequencies other than infrared frequencies. A balance is included with at least the balance pan (or platform) in the cavity. An infrared source is positioned to produce and direct infrared radiation into the cavity at frequencies other than the microwave frequencies produced by the microwave source. A lens is positioned between the infrared source and the balance pan for more efficiently directing infrared radiation to a sample on the balance pan. The lens has dimensions that preclude microwaves of the frequencies produced by the source and directed into the cavity from leaving the cavity.

In another aspect, the invention is a method of loss-on-drying content measurement. In this aspect the invention includes the steps of collimating infrared radiation towards a volatile-containing sample, and concurrently propagating microwave frequencies to the same sample.

In yet another aspect, the invention is combined infrared collimator and microwave attenuator. The collimator is formed of a plurality of adjoining cells, open at both ends and oriented with the open ends of each cell generally aligned substantially parallel to one another. The interior walls of the cells have surfaces that are sufficiently specular to reflect electromagnetic radiation in the infrared frequencies; the cells have a length-to-opening ratio sufficient to attenuate electromagnetic radiation within the microwave frequencies.

The foregoing and other objects and advantages of the invention and the manner in which the same are accomplished will become clearer based on the followed detailed description taken in conjunction with the accompanying drawings.

DETAILED DESCRIPTION

Figure 1:
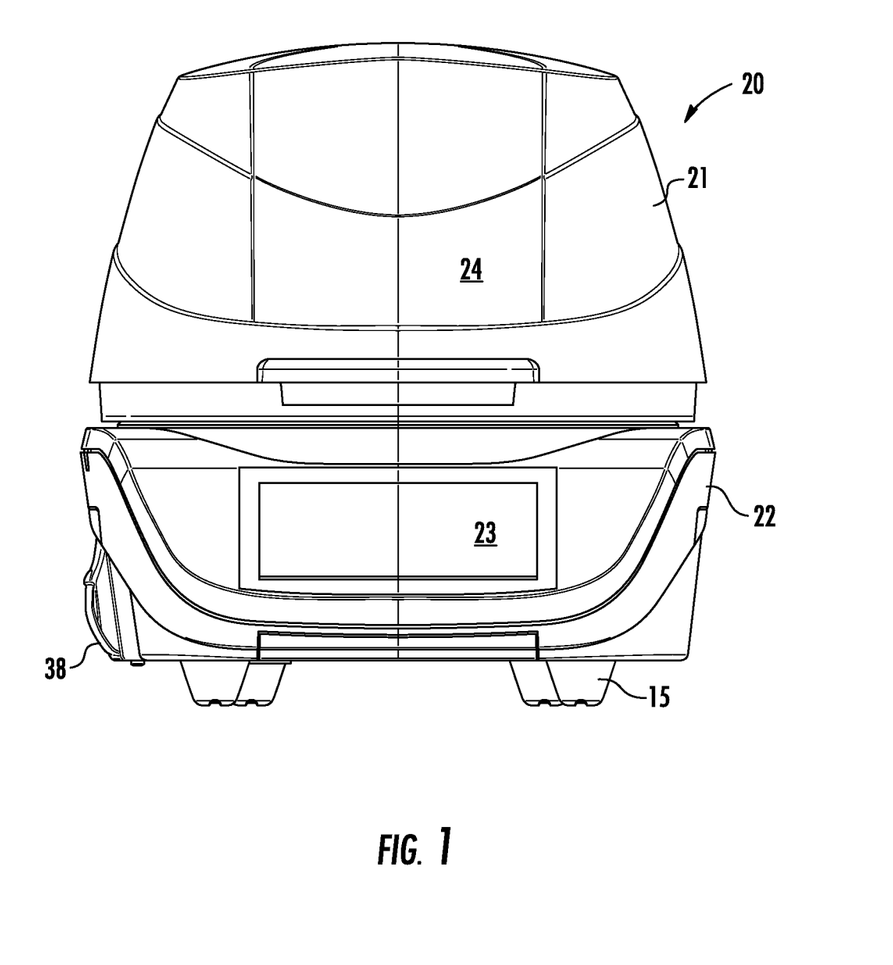
FIG. 1 is a front elevational view of an instrument according to the invention.

FIG. 1 is a perspective view of an instrument according to the present invention and broadly designated at 20. FIG. 1 illustrates an upper housing 21, a lower housing 22, and an input/output control 23 shown in the form of a touch screen. A latch 24 is part of the upper housing 21 and, as described further herein, permits access to the infrared lamps of this illustrated embodiment.

Figure 2:
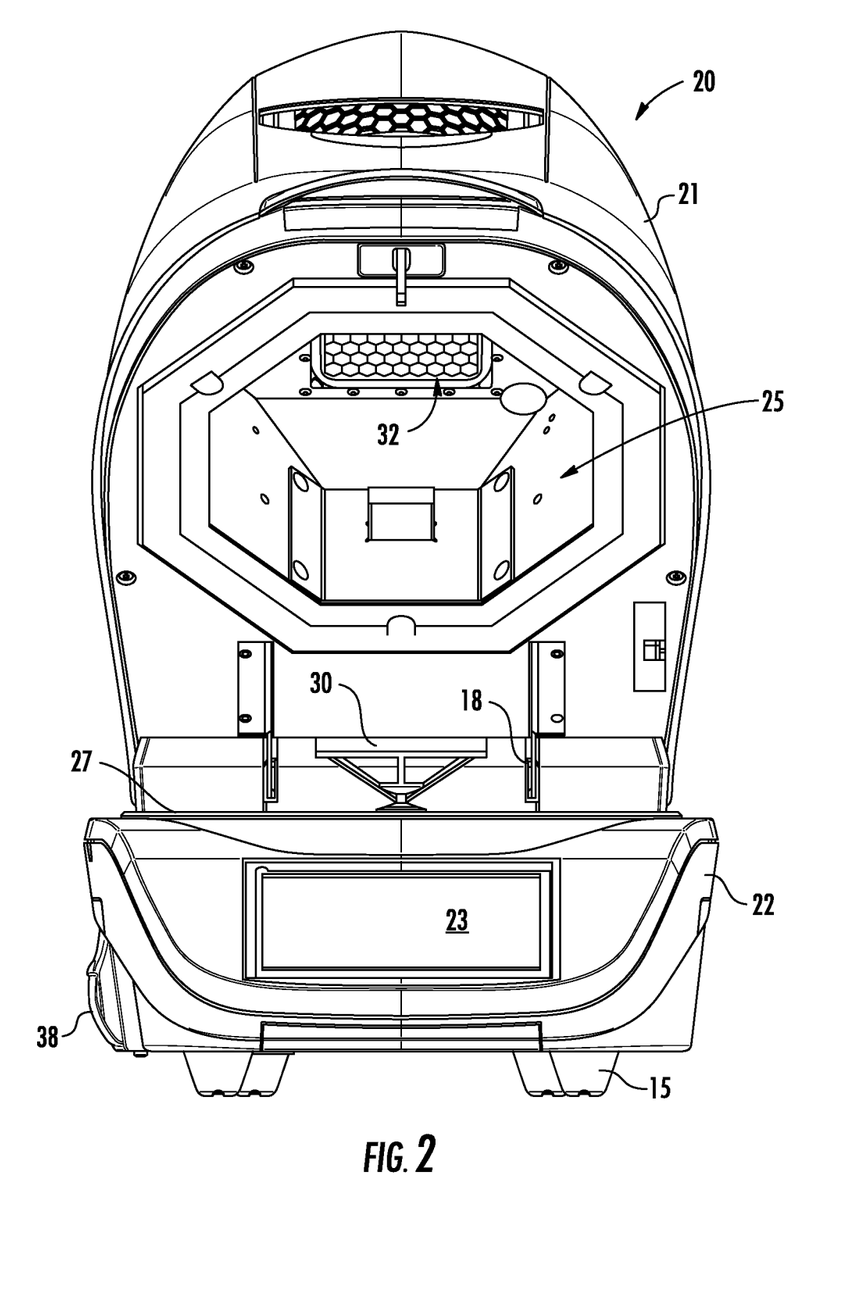
FIG. 2 is a front perspective view of the instrument of FIG. 1 opened to illustrate the cavity portion and the balance pan.

FIG. 2 illustrates the instrument 20 in partial perspective view with the housing opened on the hinges 18 to show portions of the interior. In particular, FIG. 2 illustrates the cavity 25 in the form of its upper specially shaped chamber 26 and the cavity floor 27. The instrument 20 includes a balance, more details of which will be described with respect to other drawings, but that has at least the balance pan 30 in the cavity 25 just above the cavity floor 27.

Figure 3:
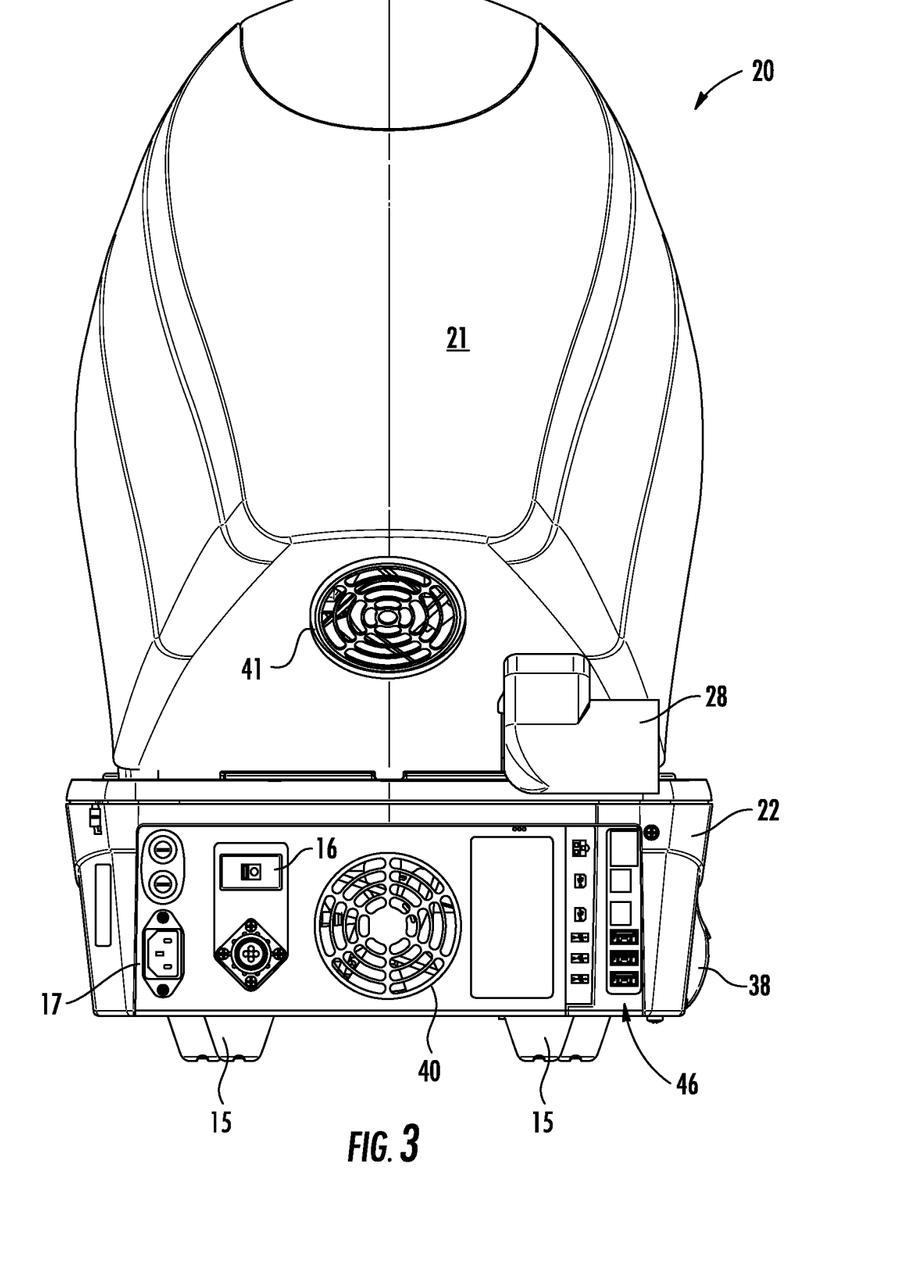
FIG. 3 is a rear perspective view of the opened instrument of FIG. 2.

FIG. 3 is a rear elevational view of the instrument 20 illustrating the upper housing in the open position. FIG. 3 illustrates a number of items in common with other figures including the upper housing 21—and the lower housing 22. FIG. 3 also illustrates a plurality of network connections 46, and a plurality of pedestal feet 15 upon which the lower housing 22 and the remainder of the instrument 20 rest. FIG. 3 also illustrates that an on-off switch 16 can be positioned at the rear of the instrument 20 along with the plug 17 for a power cord.

The network connectors can be selected by those of skill in this art without undue experimentation, but the instrument and processor are in most cases consistent with Ethernet connections, or 802.11 wireless transmissions ("WiFi") or short range radio frequency connections for which the 2.4 gigahertz standard ("Bluetooth") is widely accepted and used. Again, the choices are exemplary rather than limiting.

FIG. 3 also illustrates an exhaust elbow 28 that is connected to the cavity 25 illustrated in other drawings and which is used to draw volatile gases and water vapor from the cavity during the heating process.

Figure 4:
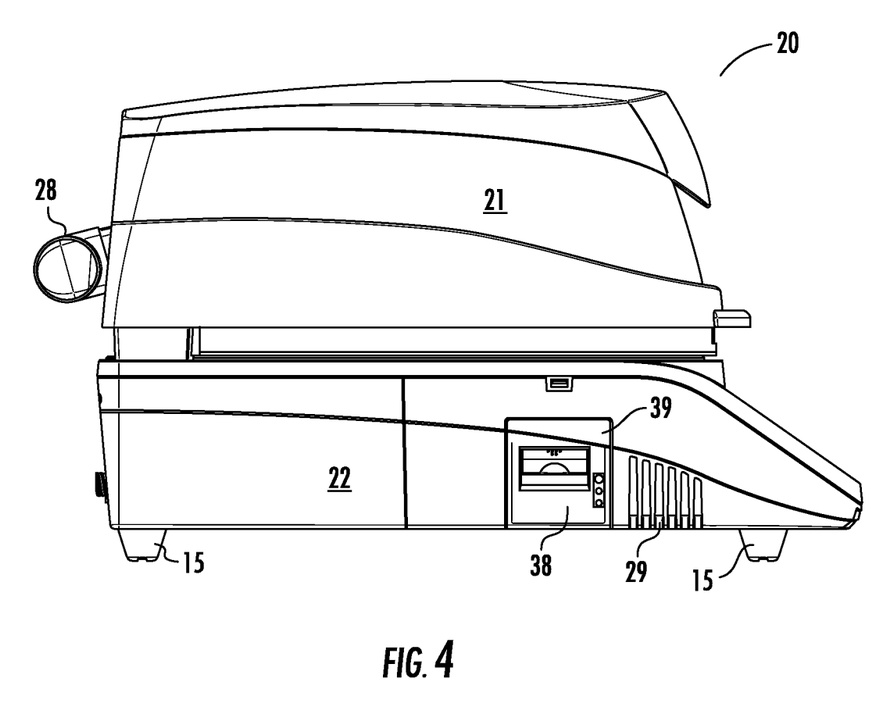
FIG. 4 is a side elevational view of an instrument according to the present invention.

FIG. 4 is a side elevational view of the instrument 20 illustrating a number of the same items as FIGS. 1-3 and that additionally illustrates the vents 29 as well as a printer 38 adjacent the vents 29. The printer has a door 39 that flips down so that paper rolls can be added as desired or necessary.

Figure 5:
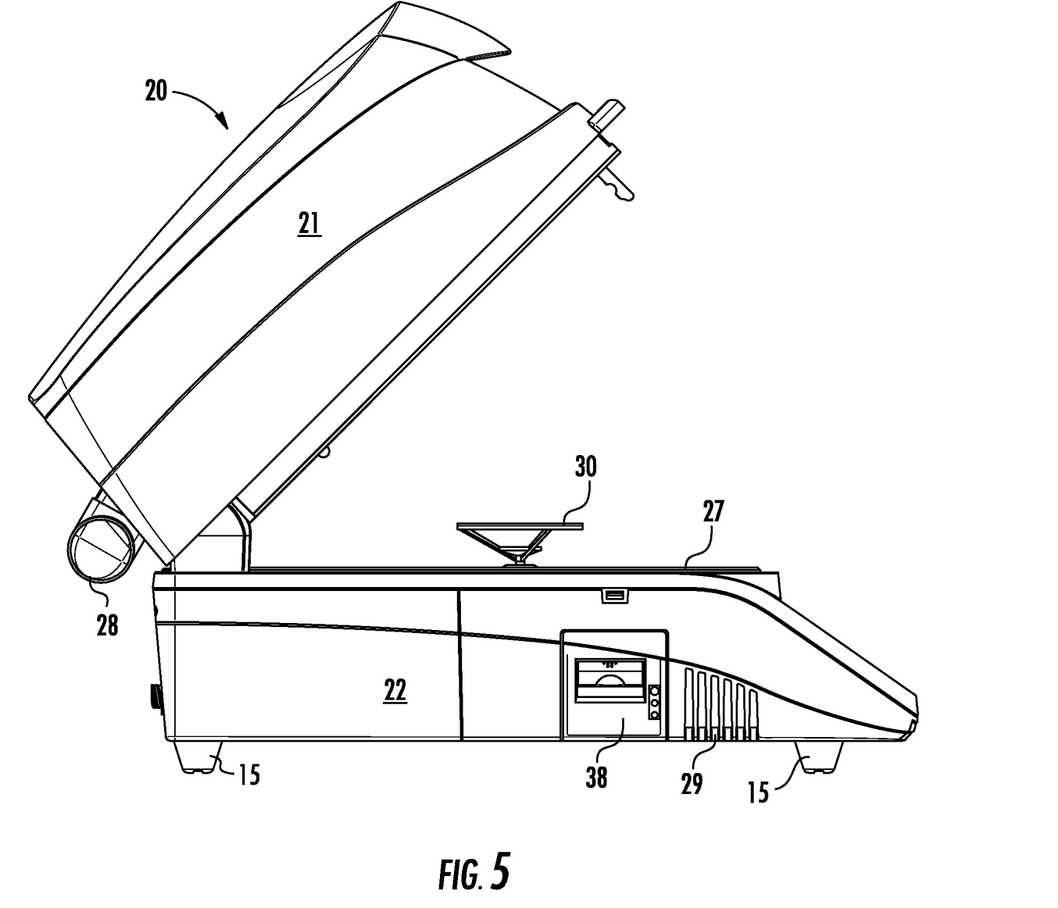
FIG. 5 is a side elevational view corresponding to FIG. 4, but with the instrument open.

FIG. 5 has the same orientation as FIG. 4, but showing the instrument in the open position. FIG. 5 accordingly illustrates the balance pan 30, and the cavity floor 27.

Figure 6:
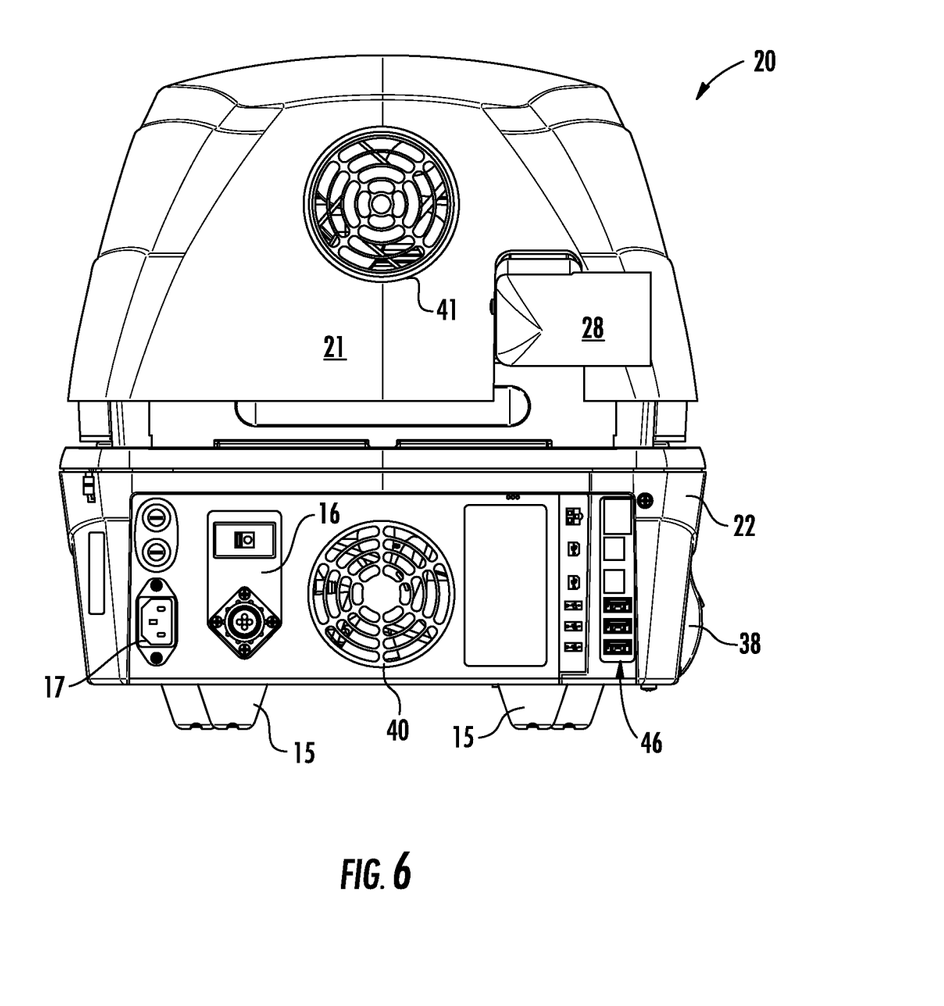
FIG. 6 is a rear elevational view of the instrument in the closed orientation.

FIG. 6 is a rear elevational view of the instrument 20 that illustrates the same items as FIG. 3, but with the instrument in the closed position.

Although the use of a cavity is primarily expected for microwave techniques, the use of the cavity with infrared radiation also has advantages independent of the use of microwaves. As one advantage, the cavity provides a defined thermal environment for the sample and thus raises the heating efficiency. As another advantage, when the cavity is made of a material that reflects infrared radiation (such as metal, which is typical), the cavity likewise enhances the overall heating efficiency. As yet another advantage, when using a sensitive balance for which even small air currents can give a false or inaccurate reading, such as described in commonly assigned U.S. Pat. No. 6,521,876, the cavity provides a shield against exterior air movement and again increases the accuracy and precision of the weighing step and thus increases the overall efficiency.

When microwaves are also used in the instrument, the cavity provides the desired shielding against undesired propagation of microwaves outside of the instrument, and some cavity designs help support a single mode of microwave radiation for one or more of the frequencies generated by the source. Nevertheless, a cavity that is closed to radiation entering or leaving for microwave purposes is as a result usually opaque to visible or infrared frequencies, and some opening must be provided for visible or infrared frequencies in a dual source instrument.

Figure 7:
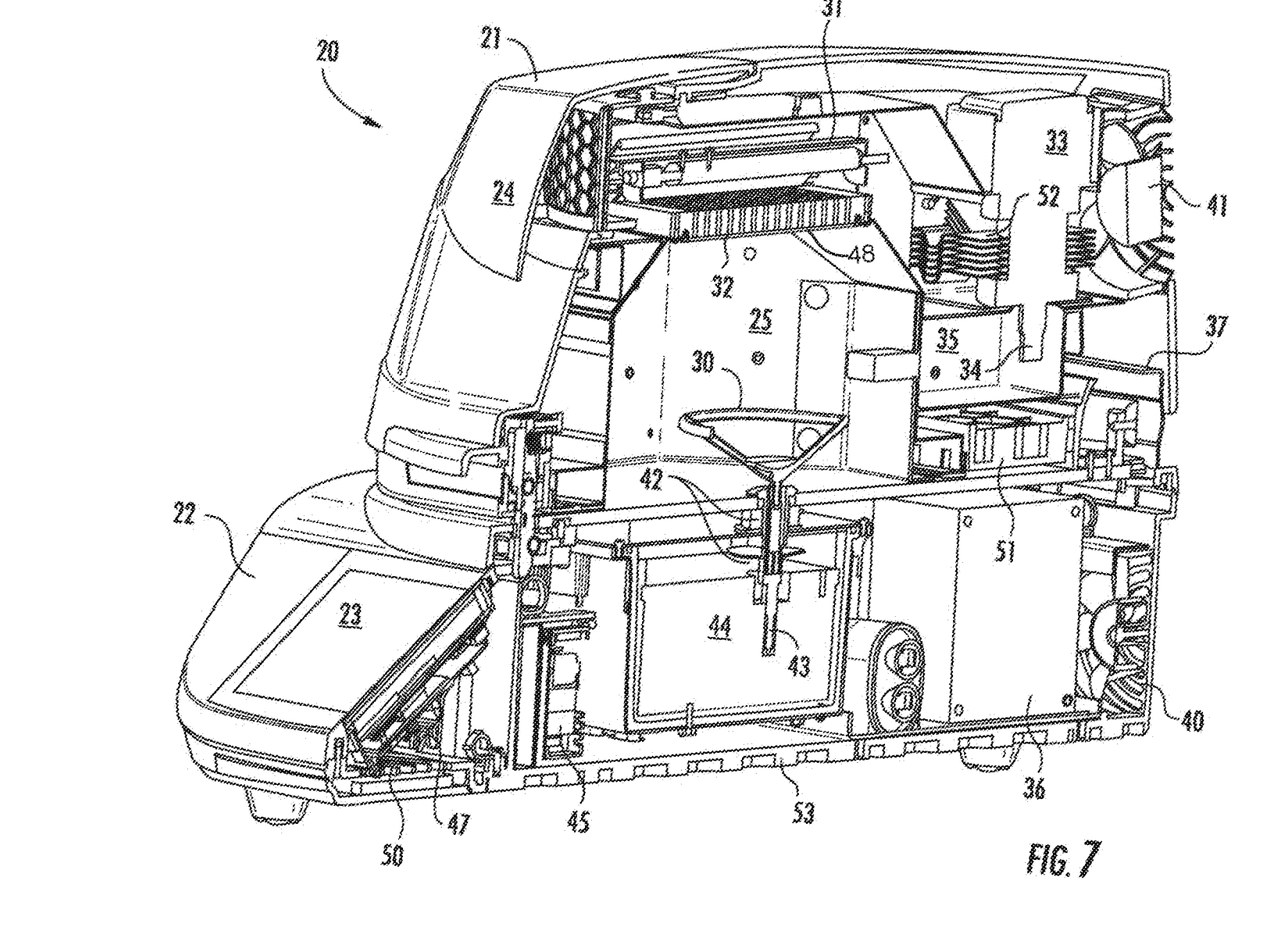
FIG. 7 is a partial cross-sectional, partial perspective view of the interior of the instrument.

FIG. 7 is a partial cross-sectional, partial perspective view of the instrument 20 according to the invention. FIG. 7 illustrates the same items as in FIG. 1 and FIG. 2, but with additional interior detail. It will be understood by the skilled person that much of the interior detail is straightforward and need not be described in detail herein other than as the parts fit together in an exterior housing of a particular size and shape. That said, a pair of infrared lamps 54 (FIG. 9) are positioned near the top of the upper housing 21 and are covered with an infrared reflector 31 typically (although not necessarily) formed of metal and typically having a highly reflective surface. Of these characteristics, the reflective surface and the ability to be in close proximity to the infrared lamps 54 is functionally most important, and other materials such as ceramics or engineering polymers can potentially be incorporated provided they can withstand the ambient heat generated by the lamps and otherwise do not interfere with the function of the lamps, or any other portions or operations of the instrument.

Figure 9:
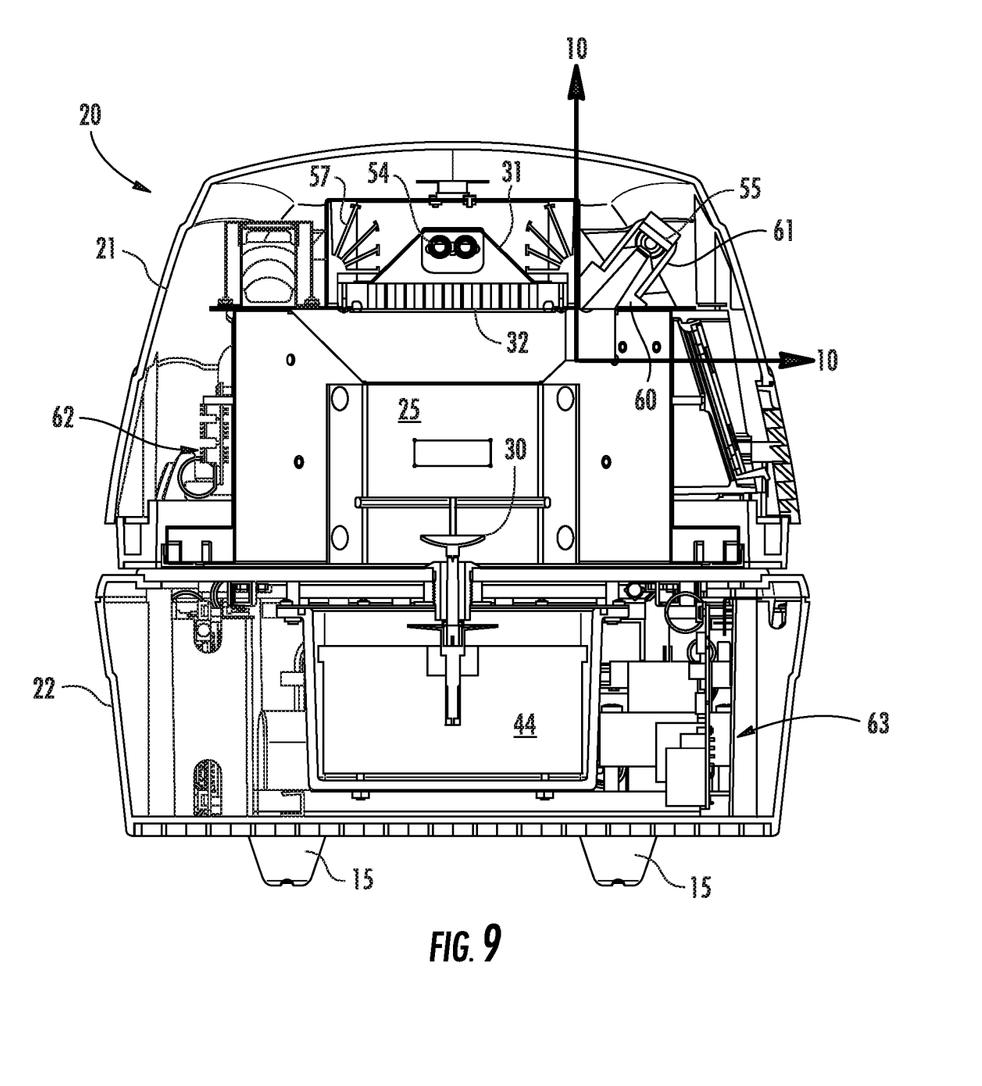
FIG. 9 is a direct cross-sectional view of the instrument perpendicular to FIG. 12.

A lens illustrated as the honeycomb shaped collimator 32 is positioned in an upper wall of the cavity 25 between the lamps 54 and the balance pan 30. The lens 32 serves to direct infrared radiation more efficiently at (or to) the balance pan 30 position rather than simply flooding the cavity with infrared radiation. Focusing the infrared radiation in this manner has at least several benefits, including but not necessarily limited to, heating the sample more efficiently (and thus using less energy) and minimizing or eliminating any interference when temperature control is carried out using an infrared thermal sensor (e.g., 59; FIG. 9).

To repeat a salient point, the term "lens" is used herein in the sense of an item or device that directs or focuses radiation, including frequencies (wavelengths) other than visible light, such as infrared or microwave radiation. The reflective collimator described and claimed herein falls within this dictionary definition.

FIG. 7 also illustrates the microwave source 33 which in the illustrated embodiment is a magnetron, but which (depending upon costs and other factors) could include a klystron or an IMPATT diode. An antenna 34 projects microwaves into the waveguide 35 and from the waveguide 35 into the cavity 25. The power supply 36 provides power to the microwave source 33 and these portions of the instrument 20 are cooled as necessary by one or more fans 40, 41. An infrared transparent window 48 separates the flow of cooling air from the balance pan 30. A switching power supply (e.g., commonly assigned U.S. Pat. No. 6,288,379) can offer additional precision and control.

As some additional details, FIG. 7 illustrates that the balance pan 30 is in the form of an open framework that will support a rigid or semi rigid sample pan; i.e., the balance pan itself does not need to be a solid planar object. The balance pan 30 is supported by a shaft 42.

In most embodiments, including this illustrated embodiment, the balance 44 is a load cell of the strain gauge type, although this is illustrative rather than limiting of the invention. A mechanical scale is acceptable assuming that it is accurate, precise, reliable, and properly calibrated and maintained. The method of operation can involve either the use of a weight balancing mechanism or the detection of the force developed by mechanical levers.

A processor and its associated electronics are illustrated at 45. The processor is in communication with the balance, the infrared source 54, the microwave source 33 the temperature sensor 55, and the input and output control 23. The electronics for the touch screen input control 23 are illustrated at 47. FIG. 7 also shows reinforcing structures throughout the instrument such as the supporting structure floor 53 under the instrument, the grid 50 below the touch screen 23, and the grid 51 above the power supply 36. A plurality of radiating fins 52 on the magnetron 33 help to reduce heat accumulation as do the heat sink fins 57 (FIG. 8) near the infrared lamps 54.

Figure 8:
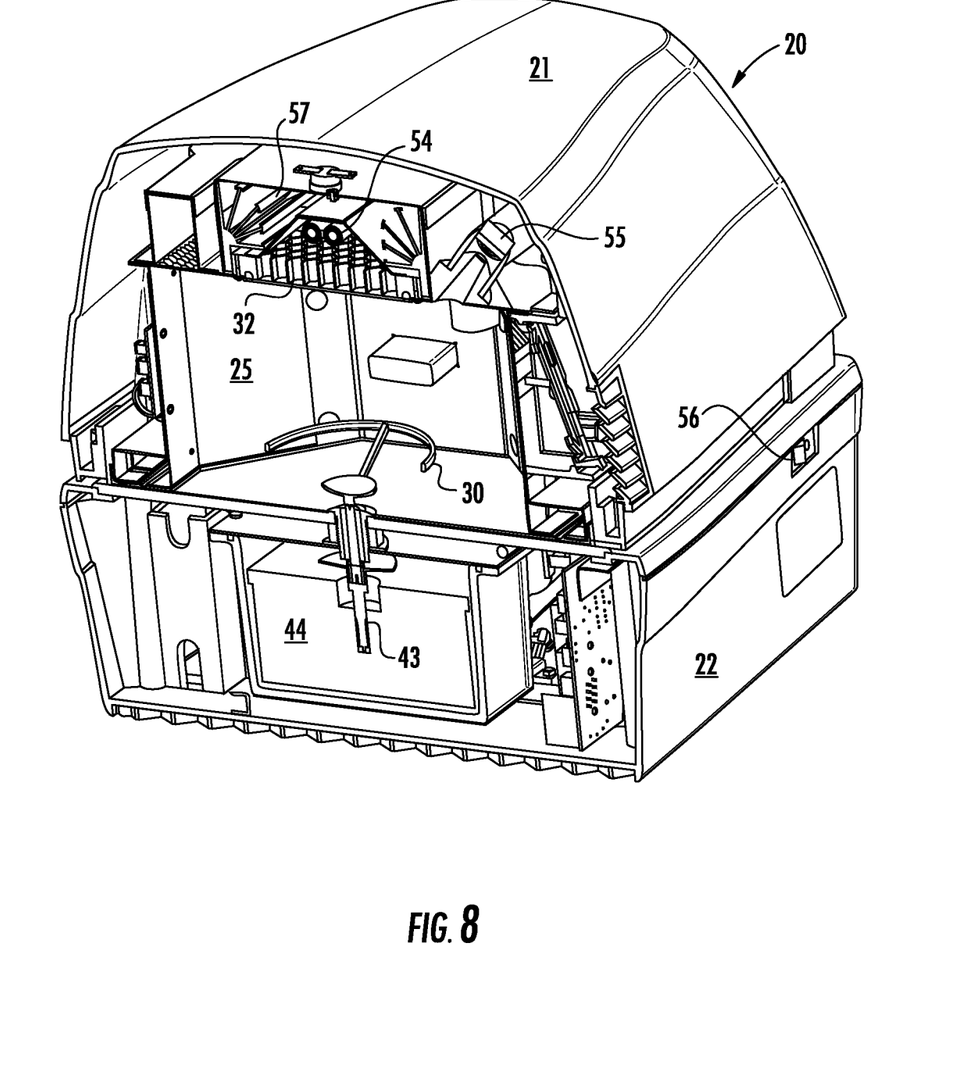
FIG. 8 is a partial perspective, partial cross-sectional view oriented perpendicularly to FIG. 7 of an instrument according to the invention.

FIG. 8 is another partial perspective, partial cross-sectional view of the instrument 20. FIG. 8 illustrates many of the same items as FIGS. 1-3, but is particularly illustrative of the reflector 31, the infrared source shown as a pair of infrared lamps 54, and the temperature sensor illustrated as the infrared detector 55. As FIG. 8 illustrates, the detector 55 focuses on the sample pan 30, and thus on a sample during use. The infrared detector 55 is in communication with the processor 45 so that the temperature of the sample on the pan 30 can be taken into consideration as drying proceeds. FIG. 8 also illustrates an on-off switch 56 located near the rear of the lower housing 22.

Figure 12:
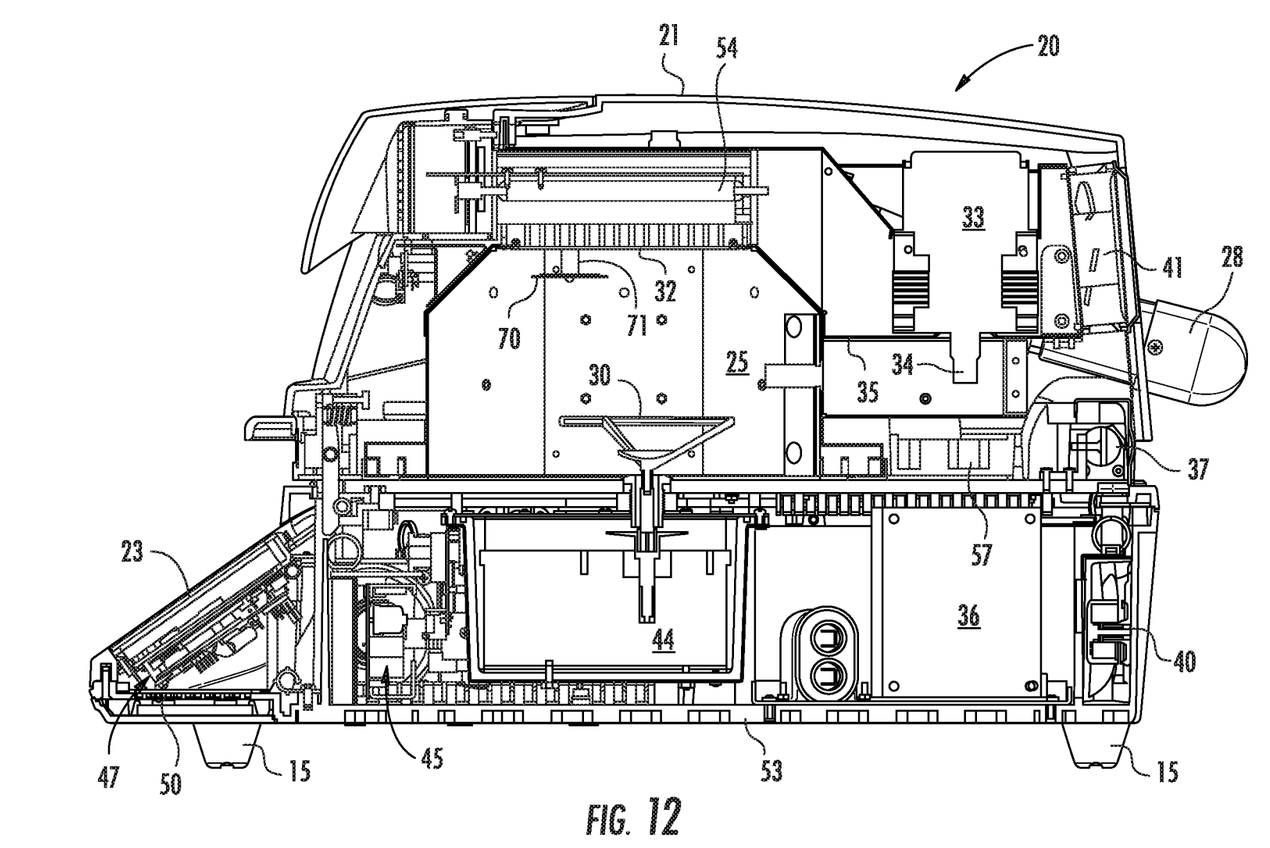
FIG. 12 is a cross-sectional view taken perpendicularly to the cross-section of FIG. 9.

FIG. 9 is a cross-sectional view generally perpendicular to the longitudinal view of FIG. 12. FIG. 9 includes many of the same elements as the previous drawings, but also illustrates details of the infrared lamps 54, the infrared reflector 31, a plurality of heat sink fins 57, and portions of the infrared detector 55, which in turn is illustrated in greater detail in FIG. 10. The portions of the infrared detector 55 illustrated in FIG. 9 include a mount 60 and a collar 61. FIG. 9 also broadly illustrates portions of the lamp electronics 62, and portions of the processor and balance electronics 63.

For reasons well understood to those familiar with this art, the infrared temperature detector 55 is positioned to target a sample on the balance pan 30. In particular, the nature of the detector and the distance from the detector to the source (in this case a heated sample) help increase the efficiency and precision of the results from such detectors, and these factors are likewise well understood in the art.

The processor 45 is in communication with the infrared source lamps 54, the microwave source 33, and the temperature detector 55, so that the application of radiation (infrared or microwave or both) to a sample can be moderated in response to the detected temperature. Such temperature detection and response provides precise control over the sample heating, and helps keep the temperature within a range that drives off moisture and other volatiles without creating undesired decomposition that would produce inaccurate results based on the measured weight change of that sample.

Figure 10:
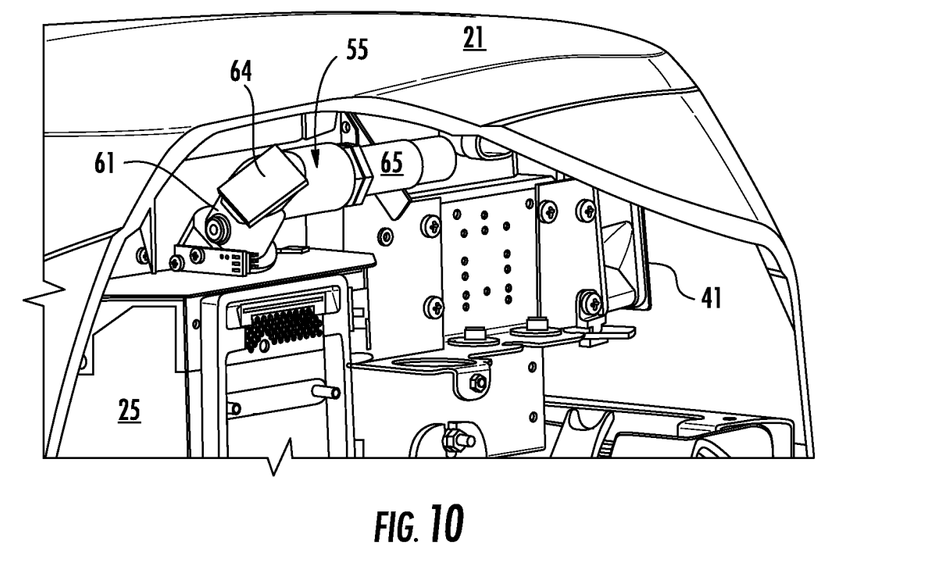
FIG. 10 is an enlarged view of a portion of the interior of the instrument illustrating the infrared sensor temperature.

FIG. 10 is a cutaway perspective view taken generally along the segment 10-10 in FIG. 9. FIG. 10 illustrates the infrared detector 55 in more detail, particularly the collar 61 and a mirror 64 that directs infrared radiation from the cavity 25 to reflect into the detector diode (not shown) within its housing 65.

Figure 11:
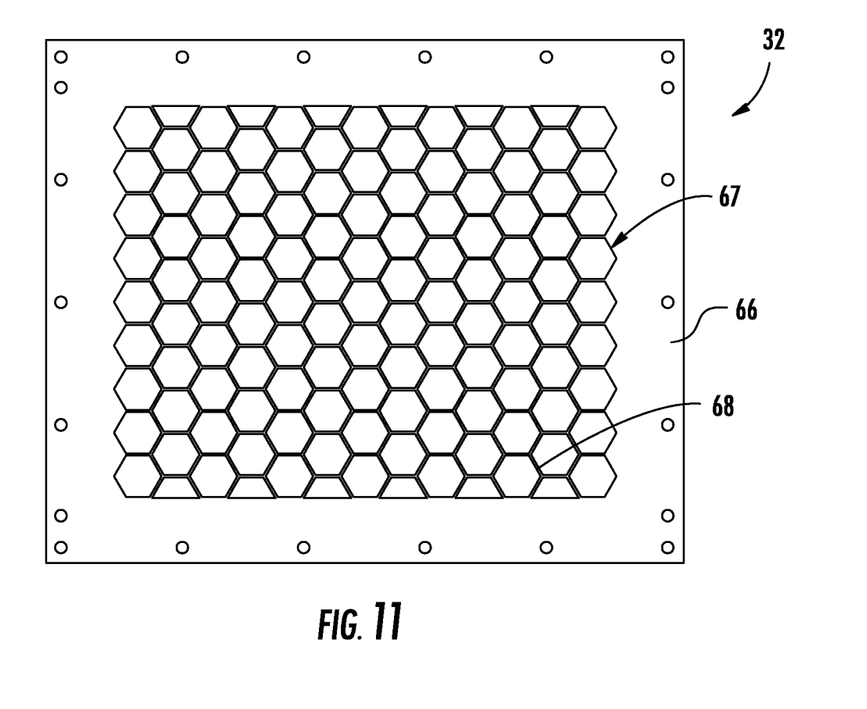
FIG. 11 is a segregated enlarged view of the collimator according to the invention.

FIG. 11 is a segregated perspective view of the collimator 32 according to the present invention. In the illustrated embodiment, which has been found to be advantageous, the collimator is formed of a frame 66 and a plurality of smaller hexagonally shaped open cells 67 within the perimeter defined by the collar 66. Because the collimator serves two functions, it is engineered and proportionately sized to meet both functions. As a first function, the collimator re-directs (or more closely directs) infrared radiation from the lamps 54 and the reflector 31 to the portion of the cavity 25 at which the sample will be positioned. In the illustrated embodiment, this position is predominantly defined by the balance pan 30.

Therefore, the size of the cells 67 (length and width), their surface, and the material from which they are made, all must be consistent with their infrared radiation related function.

As a concurrent function, however, the collimator must preclude microwave energy having frequencies produced by the source 33 from leaving the cavity 25. Therefore, the size and material of the cells 67 must meet that function as well. The function is referred to as attenuation, and an item with such a function is informally referred to as a choke. In order to serve as a choke, the length (longer dimension) of the opening structure must exceed the diameter (or open area) of the structure by a defined proportional amount. The use and sizing of such attenuators is well understood in the art and need not be discussed herein in detail other than to note that an attenuator in the form of a cylinder should have a diameter smaller than the propagated wavelength ($\lambda$) and a length that is at least one-fourth of the propagated wavelength.

Accordingly, the cells 67 are open at both ends and standing alone are oriented with the open ends of each of the cells generally aligned substantially parallel to one another. The interior walls 68 of the cells 67 have surfaces that are sufficiently specular to reflect electromagnetic radiation in the infrared frequencies, and the cells 67 have the length-to-opening ratio that is sufficient to attenuate electromagnetic radiation within the microwave frequency range.

As examples of relevant infrared sources, quartz-halogen lamps emit wavelengths predominately at about 3.5 microns ($\mu$m) and tungsten lamps at about 2.5 $\mu$m. The detector 55 can be selected or designed to offer the most sensitivity within a particular range. In exemplary embodiments, the detector 55 measures radiation from the sample in the range of about 8-15 $\mu$m. By virtue of this selection, the frequency (or corresponding wavelength) of the infrared source differs from both the microwave frequencies and from the infrared detector frequencies, thus enhancing the accuracy and precision of the temperature measurement and in turn of the feedback control.

Expressed in this manner, the interior wall surfaces 68 will reflect infrared radiation having wavelengths of between about 1 microns ($\mu$m) and 1 millimeter (mm) and the cells 67 will attenuate microwave radiation having wavelengths between about 1 mm and 1 meter. In most cases the combined collimator and attenuator has cells formed of metal.

It will be noted, of course that for microwave attenuation purposes, the cell walls 68 do not need to be specular, and that for collimating purposes, the cells 67 do not need to meet the microwave attenuation ratio. The combination of these functions thus provides an unexpected benefit for both purposes that neither an attenuator nor an infrared collimator would provide if standing alone.

The instruments described herein are typically designed to operate in the S band (2-4 gigahertz; 7.5-15 millimeters) based on regulation of electromagnetic radiation in the United States and elsewhere. Based upon that, in the illustrated embodiment, the overall frame has dimensions of about 14 centimeters by about 12 centimeters, and the hexagonal openings are approximately 0.9 centimeters across and about 1 centimeter long. In one sense, if the proportional requirements for infrared radiation and microwave attenuation are met, different sizes can be selected based on available space, the size and positioning of the lamps, and the microwave frequencies being propagated into the cavity.

FIG. 12 is a full cross sectional view longitudinally through the instrument and illustrates everything in FIG. 7 along with several additional items. In particular, FIG. 12 illustrates a microwave stirring blade 70 mounted on a small rotating shaft 71. FIG. 12 also provides an excellent illustration of the shape of the cavity 25 which can be the same or similar to the shape described in commonly assigned U.S. Pat. No. 6,521,876, the contents of which are incorporated entirely herein by reference.

In another aspect the invention includes a method of loss-on-drying content measurement that collimates infrared radiation towards a volatile-containing sample while concurrently propagating microwave frequencies to the same sample. In the method the microwaves are attenuated at a collimator that collimates the infrared radiation used to dry the sample. Based on that, the microwave attenuator has the proportional dimensions required to attenuate the microwave frequencies being propagated.

As is fundamental to loss-on-drawing techniques, the method further includes the steps of weighing the sample before starting either of the collimating or microwave propagating steps, and weighing is also carried out during the heating and microwave steps. In this manner the sample can be dried to completion and once a weighing step is carried out after completion, the percentage of volatiles in the material can be easily calculated.

As those familiar with microwave techniques are aware, however, in many cases the loss of moisture and volatiles during the heating process will rapidly assume an asymptotic curve from which an end point (i.e., mathematically representative of a totally dry sample) can be calculated once several (two or three are often sufficient) measurements are taken during drying. The processor included with the instrument can provide this function as well; see, U.S. Pat. No. 4,457,632.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A volatile content analysis instrument comprising:
an upper housing and a lower housing;
a cavity in said upper housing with eight vertical sides made of a material that reflects both microwave and infrared radiation;
a microwave source in said upper housing selected from the group consisting of magnetrons, klystrons, and IMPATT diodes;
said microwave source being positioned to produce and direct microwaves into said cavity at frequencies other than infrared frequencies;
a power supply located in said lower housing for providing power to said microwave source;
at least one fan located in the rear of said upper housing for transferring, as necessary, heat generated by said microwave source in said upper housing to cooling air;
at least one fan located in the rear of said lower housing for transferring, as necessary, heat generated by said power supply in said lower housing to cooling air;
an exhaust in said upper housing connected to said cavity for drawing volatile gases and water vapor from said cavity;
a balance with at least a balance pan in said cavity wherein said balance includes a balance pan on a shaft and said balance pan includes an open frame that will support both rigid and semi-rigid sample pans;
an infrared temperature detector in said upper housing positioned to target a sample on said balance pan wherein said infrared temperature detector measures radiation from a sample in the wavelength range of between about 8 and 15 μm;
an infrared source in said upper housing that emits wavelengths at between about 2.5 and 3.5 μm that is positioned to produce and direct infrared radiation into said cavity concurrently with microwaves from said microwave source at frequencies other than the microwave frequencies produced by said microwave source and other than the frequencies measured by said infrared temperature detector;
an infrared reflector in said upper housing in close proximity to said infrared source that does not interfere with the function of said infrared source and that has a highly reflective surface made of material that can withstand the ambient heat generated by said infrared source;
a plurality of heat sink fins in said upper housing positioned near said infrared source to reduce heat accumulation;
a lens in upper portions of said cavity between said infrared source and said balance pan, said lens having a plurality of hexagonally shaped adjoining cells open at both ends, said cells having metal interior surfaces sufficiently specular to reflect, direct and collimate infrared radiation from said infrared source and said infrared reflector to a sample on said balance pan;
said cells in said lens having dimensions that preclude microwave radiation of the frequencies produced by said microwave source and directed into said cavity from leaving said cavity through said lens, and said cells in said lens having interior wall surfaces that reflect infrared radiation having wavelengths between about 1 micron and 1 millimeter, and said cells in said lens attenuating microwave radiation having wavelengths between about 1 millimeter and 1 meter;
a microwave stirring blade mounted on a rotating shaft in upper portions of said cavity below said lens;
an input and output control positioned in said lower housing; and
a processor in said lower housing in communication with said balance, said input and output control, said infrared source, said microwave source, and said infrared temperature detector for moderating the application of radiation to a sample in response to the detected temperature.

* * * * *